United States Patent [19]

Suarato et al.

[11] 4,345,068

[45] Aug. 17, 1982

[54] PROCESS FOR THE PREPARATION OF 4'-EPIDAUNORUBICIN, 3',4'-DIEPIDAUNORUBICIN, THEIR DOXORUBICIN ANALOGS, AND INTERMEDIATES USED IN SAID PROCESS

[75] Inventors: Antonio Suarato; Sergio Penco; Federico Arcamone, all of Milan, Italy

[73] Assignee: Farmitalia Carlo Erba S.p.A., Milan, Italy

[21] Appl. No.: 164,088

[22] Filed: Jun. 30, 1980

[30] Foreign Application Priority Data

Nov. 22, 1979 [GB] United Kingdom ................. 7940457

[51] Int. Cl.$^3$ ...................... C07H 15/24; A61K 31/71
[52] U.S. Cl. .................................. 536/17 A; 424/180
[58] Field of Search ........................... 536/17 A, 17 R; 424/180

[56] References Cited

U.S. PATENT DOCUMENTS 4,039,663  8/1977  Arcamone et al. ............... 536/17 A
4,112,076  9/1978  Arcamone et al. ............... 536/17 A Primary Examiner—Blondel Hazel
Attorney, Agent, or Firm—Berger & Palmer

[57] ABSTRACT

Disclosed is a process for preparing the known antitumor glycosides: 4'-epidaunorubicin, 3',4'-diepidaunorubicin, and their doxorubicin analogs by oxidizing the C-4' hydroxyl group of N-protected daunorubicin to form certain novel intermediates having a 4'-keto configuration, followed by reduction of the keto group with NaBH$_4$ and mild alkaline hydrolysis to remove the N-protecting acyl groups.

7 Claims, No Drawings

PROCESS FOR THE PREPARATION OF 4'-EPIDAUNORUBICIN, 3',4'-DIEPIDAUNORUBICIN, THEIR DOXORUBICIN ANALOGS, AND INTERMEDIATES USED IN SAID PROCESS

BACKGROUND OF THE INVENTION

1. Field of the Invention

The present invention relates to a new process for the synthesis of the known antitumor antibiotics 4'-epidaunorubicin, 3',4'-diepidaunorubicin and their doxorubicin analogs. The invention also relates to certain novel intermediates used in the process.

2. The Prior Art

U.S. Pat. No. 4,039,663 discloses 4'-epidaunorubicin and its use in treating certain mammalian tumors. U.S. Pat. No. 4,058,519 similarly discloses 4'-epidoxorubicin and its use. Finally, U.S. Pat. No. 4,112,076 discloses in like manner 3',4'-diepidaunorubicin and 3',4'-diepidoxorubicin.

The starting material for the process of the invention is N-trifluoroacetyl daunorubicin, a known material whose preparation from daunorubicin (also known) is described in U.S. Pat. No. 3,803,124.

SUMMARY OF THE INVENTION

In one aspect thereof, the present invention provides a new process for the preparation of the known daunorubicin analogs of the formula:

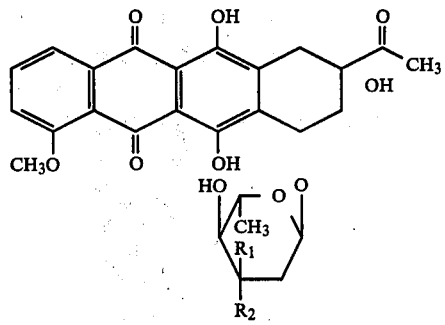

wherein
(a) $R_1$ is hydrogen and $R_2$ is $NH_2$; or
(b) $R_1$ is $NH_2$ and $R_2$ is hydrogen.

The process proceeds through certain novel key intermediates which are 4'-keto-N-protected daunorubicin compounds (III a, b-IV a, b) which also form part of the invention. Other novel intermediates are also involved in the process and they too are within the scope of the invention.

According to the process of the invention, which is schematically shown below, N-protected daunorubicin derivatives (I, II) are converted to 4'-epi-daunorubicin (VII) and 3',4'-diepidaunorubicin (VIII). Compounds VII and VIII can then be converted to the corresponding doxorubicin analogs.

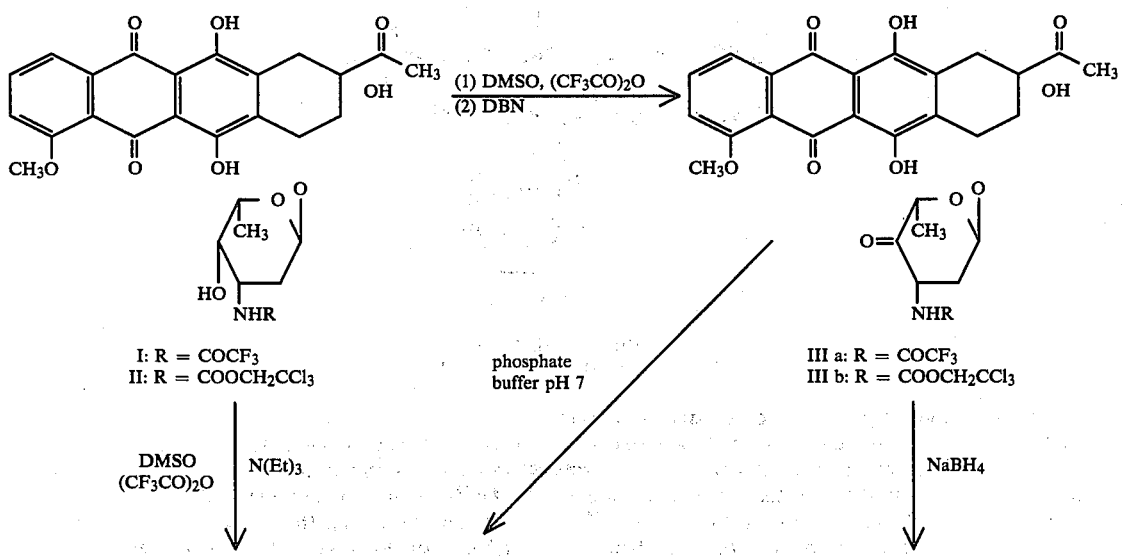

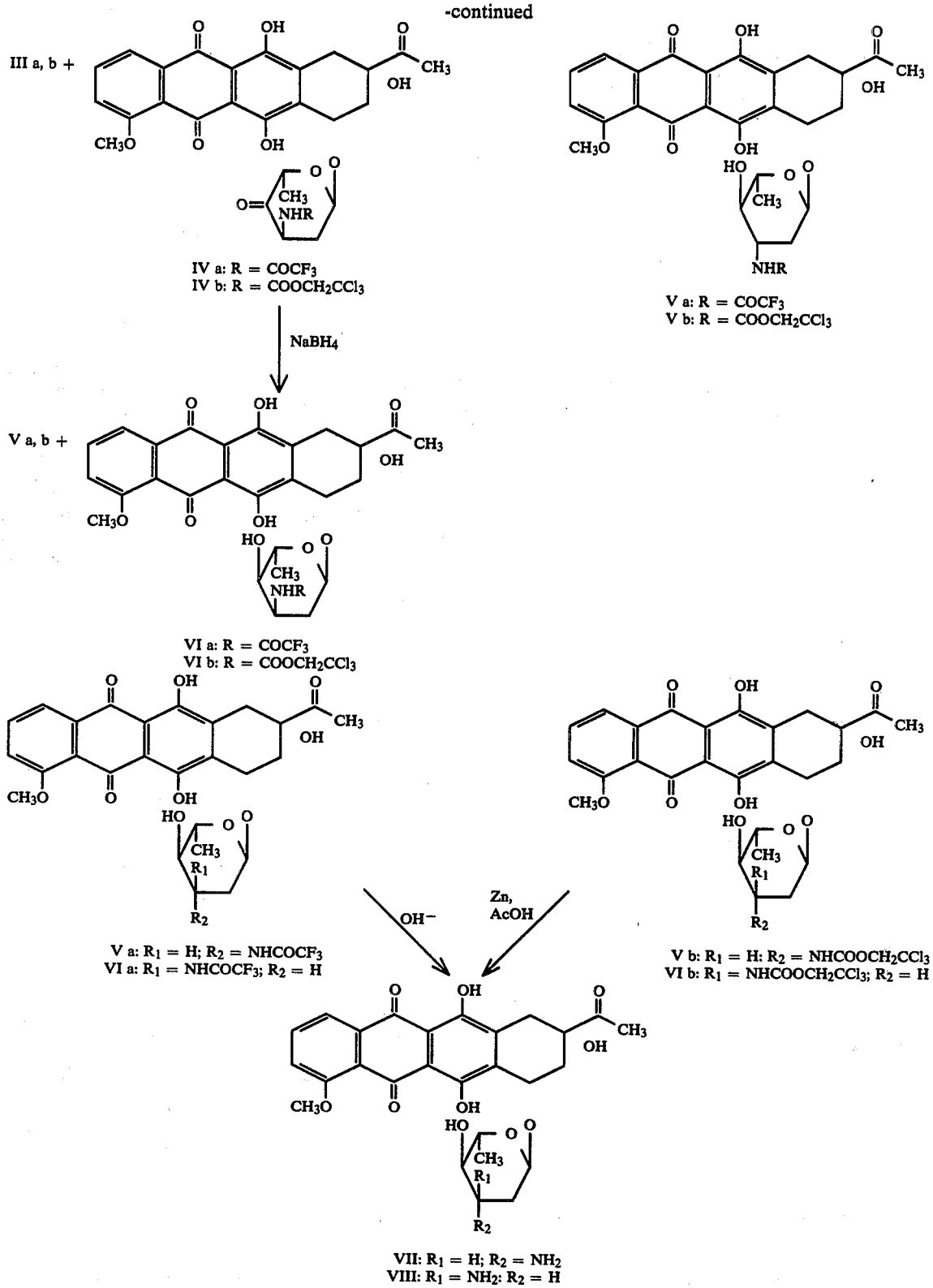

According to the process, in order to effect oxidation of the hydroxyl group at the C-4' position of daunorubicin it is necessary to first protect the amino group of the sugar moiety with a suitable protecting group, such as for example an acyl derivative or a Schiff base. The suitably N-protected daunorubicin (I or II) is then subjected to an oxidative reaction with activated dimethylsulfoxide (K. Omura and D. Swern, Tetrahedron 1978, 34, 1651–1660). It is noteworthy that as shown in the foregoing schematic, the use of a bulky base, such as 1,5-diazobicyclo (4.3.0) non-5-ene (DBN), in the basification step of the oxidation gives the ketones IIIa and IIIb in high yield, whereas the use of triethyl amine in place thereof selectively affects the asymmetric C-3' carbon atom giving a mixture of epimeric ketones at the C-3' position, namely IIIa, b-IV a,b in an approximate ratio of 1:1. Moreover the above mentioned epimerization can be achieved by simply treating ketones IIIa and IIIb with silica gel buffered at pH 7 with phosphate buffer. The selective and stereospecific reduction of the carbonyl function in the sugar moiety of III, a,b-IV a,b gives the N- protected glycosides V a,b-VI a,b respectively having an L-arabino and an L-ribo configuration. Finally, the hydrolysis of the N-protecting groups affords the glycosides VII and VIII, which are isolated as the hydrochlorides.

In another aspect thereof, the invention provides the novel intermediates IIIa, IIIb, IVa, IVb, Va, Vb, VIa and VIb.

Compounds VII and VIII (as well as their doxorubicin analogs) are, as noted above, known compounds whose use in treating mammalian tumors is known from the literature.

DETAILED DESCRIPTION OF THE INVENTION AND PREFERRED EMBODIMENTS THEREOF

The starting material for the process of the present invention is daunorubicin (daunomycin), a known anti-tumor antibiotic whose preparation and use is amply described in the literature. The N-trifluoroacetylderivative (I) of daunorubicin is easily prepared in the manner described in U.S. Pat. No. 3,803,124 by reacting it with trifluoroacetic anhydride in the presence of an organic solvent, followed by the hydrolysis of the O-trifluoroacetyl groups with methanol. N-trichloroethoxycarbonyldaunorubicin (II) is prepared by treating daunorubicin (free base) in aqueous solution with trichloroethoxycarboxychloride. The oxidation of the hydroxyl groups at the C-4' position of either I or II, is effected with dimethyl sulfoxide (DMSO) activated by trifluoroacetic anhydride. This reagent is prepared in anhydrous methylene chloride, cooled, preferably to between $-50°$ and $-70°$ C. The substrate (I or II) dissolved in anhydrous methylene chloride is added to a suspension of the reagent, while keeping the temperature at $-65°$ C. in order to form the dimethylalkoxy sulfonium salt. The formation of this salt can be monitored quite readily by thin layer chromatography; the disappearance of the starting material is completed in about 30 minutes. Thereafter, a bulky base, e.g. 1,5-diazo-bicyclo (4.3.0)-non-5-ene (DBN), is quickly added to the reaction mixture which is kept at $-65°$ C. When the addition of the base is completed, the reaction mixture is neutralized with acetic acid and quenched by pouring it into an organic solvent, such as methylene chloride. The solution is then washed with water, dilute aqueous sodium bicarbonate solution and finally water. Upon evaporation of the solvent to dryness, the ketones III a and III b are obtained in quantitative yield.

On the other hand, the use of triethylamine instead of DBN leads to the formation of a mixture of the ketones III a, III b and IV a, IV b in an approximately 1:1 ratio.

The next, or reduction step is performed in a water miscible organic solvent, such as methanol or dioxane, with NaBH$_4$ with cooling to $-10°$ C. for ten minutes. Under these conditions, the reduction of the carbonyl group on the side-chain of the chromophore is minimized and the axial attachment of a hydride ion is favored, or preferred, thereby giving the corresponding glycosides having an equatorial hydroxy group at the C-4' position. When the reduction has been completed, the reaction mixture is diluted with methylene chloride and washed with water, dilute HCl, water, dilute NaHCO$_3$ and finally water. Evaporation of the solvent affords crude V a and Vb or a mixture of crude V a and V b-VI a and VI b, which are purified by chromatography on a column of silicic acid. The mild alkaline treatment removes the N-trifluoroacetyl groups from V a and VI a. On the other hand, the trichloroethoxy carboxyamido group is cleaved by treatment of V b and VI b with Zn dust in the presence of acetic acid and ethanol to form compounds VII and VIII. Subsequent treatment of compounds VII and VIII in accordance with the method described in U.S. Pat. No. 4,058,519 and U.S. Pat. No. 4,112,076 respectively affords the corresponding doxorubicin derivatives 4'-epidoxorubicin and 3',4'-diepidoxorubicin.

EXAMPLE 1

4'-Keto-N-trifluoroacetyldaunorubicin III a

To a mixture of 60 ml of methylene chloride and 5 ml of anhydrous dimethyl sulfoxide cooled to below $-60°$ C., a solution of 4 ml of trifluoroacetic anhydride in 10 ml of anhydrous methylene chloride was added over a period of 15 minutes. During the addition period a white precipitate was formed. After 15 minutes at $-60°$ C., a solution of 6.25 g of N-trifloroacetyl daunorubicin (I) in 40 ml of methylene chloride was added dropwise to the mixture at $-60°$ C. over a period of 15 minutes. The reaction mixture, while being stirred at $-60°$ C. for 30 minutes was quickly treated with 9 ml of 1,5-diazobicyclo (4.3.0) non-5-ene (DBN) while keeping the temperature at $-60°$ C. After 1 minute the reaction mixture was neutralized with the stoichiometric amount of acetic acid and then poured into 300 ml of methylene chloride. The organic phase was washed with 0.1 N HCl, an aqueous solution of NaHCO$_3$ and then with water. The organic solution after being dried over anhydrous Na$_2$SO$_4$ was evaporated to a residue to give crude 4'-keto-N-trifluoroacetyl daunorubicin (IIIa) which was purified by chromatography on a column of silica gel using the mixture chloroform:acetone (98:2 v/v) as the eluant to give 4.8 g of (IIIa):FDMS [M+]:621 PMR (CDCl$_3$): 1.37 (d, CH$_3$-C-5'), 2.38 (s, CH$_3$CO), 3.95 (s, CH$_3$O), 4.78 (broad q, C-5'-H), 5.20 (broad s, C-7-H), 5.58 (broad s, C-1'-H), 12.93 and 13.83 $\delta$ (s, phenolic protons).

EXAMPLE 2

4'-epidaunorubicin (VII)

A solution of 1.5 g of 4'-keto-N-trifluoroacetyl daunorubicin (III a) in 150 ml of methanol was cooled at $-10°$ C. and treated with 0.035 g of NaBH$_4$ dissolved in 5 ml of methanol. After ten minutes the reduction was complete, and the reaction mixture was neutralized with 0.1 N HCl, evaporated to a small volume (ca. 30 ml) under vacuum and diluted with 200 ml of methylene chloride. The organic phase was washed with water, dried over Na$_2$SO$_4$ and evaporated to a residue. The residue, which is crude 4'-epi-N-trifluoroacetyl-daunorubicin (V a), was dissolved in 50 ml of 0.1 N aqueous sodium hydroxide. The resulting solution, after standing for 30 minutes at 5° C. was treated with 0.1 N aqueous hydrogen chloride to adjust the pH to 4.5 and extracted with chloroform in order to eliminate the aglycones. Then the aqueous solution was adjusted to pH 8.6 and repeatedly extracted with chloroform. The combined chloroform extracts were dried over anhydrous Na$_2$SO$_4$, concentrated to a small volume and acidified to pH 4.5 with 0.1 N methanolic hydrogen chloride to allow crystallization of 4'-epidaunorubicin hydrochloride (VII) m.p. 199°–201°, $[\alpha]_D + 320°$ (c 0.045, CH$_3$OH).

EXAMPLE 3

N-trichloroethoxycarbonyldaunorubicin (II)

An aqueous solution of 3 g of daunorubicin hydrochloride in 180 ml of water was adjusted to pH 10 with aqueous 0.2 N NaOH and successively treated under stirring with a solution of 2 g of 2,2,2-trichloroethylchloroformate in 10 ml of acetone. The reaction mixture was kept at pH 10 by the addition of aqueous 0.2 N NaOH and after 30 minutes at room temperature, 200 ml of methylene chloride were added. The organic phase was separated, washed with two 100 ml portions of water, dried over anhydrous Na$_2$SO$_4$ and evaporated to a residue under vacuum, giving 3.1 g of N-trichloroethoxycarbonyldaunorubicin (II); TLC on kieselgel plate F$_{254}$ (Merck) using the system CHCl$_3$:(CH$_3$)$_2$CO (4:1 v/v): Rf=0.4.

PMR (CDCl$_3$): 1.33 (d, CH$_3$-C-5'), 2.38 (s, CH$_3$CO), 4.03 (s, CH$_3$O); 4.63 (s,O-CH$_2$—CCl$_3$), 5.20 (broad s, C-7H), 5.60 (broad s, C-1'-H), 13.13 and 13.92 $\delta$ (s, phenolic protons).

EXAMPLE 4

4'-Keto-N-trichloroethoxycarbonyldaunorubicin (III b)

7.04 g of N-trichloroethoxycarbonyldaunorubicin (II) were oxidized as described in Example 1 to give 4'-keto-N-trichloroethoxycarbonyldaunorubicin (III b): FDMS [M+]699. PMR (CDCl$_3$): 1.37 (d, CH$_3$-C-5'), 2.38 (s, CH$_3$CO), 4.05 (s, CH$_3$O), 4.63 (s, O—CH$_2$—CCl$_3$), 5.30 (broad s, C-7-H), 5.60 (broad s, C-1'-H), 13.12 and 13.95 $\delta$ (s, phenolic protons).

EXAMPLE 5

4'-epidaunorubicin (VII)

A solution of 1.7 g of 4'-keto-N-trichloroethoxycarbonyldaunorubicin (III b) in 200 ml of methanol was cooled to −10° C. and treated with 0.035 g of NaBH$_4$. After ten minutes the reduction was complete. The reaction mixture was evaporated to a residue under vacuum and the resulting residue, dissolved in 200 ml of methylene chloride, was washed with water. The residue obtained after evaporation of the solvent was dissolved in 120 ml of a mixture of ethanol-methanol (3:1 v/v) and treated under stirring with 1.5 g of zinc dust which had been previously treated with aqueous 0.1 N hydrogen chloride, in the presence of glacial acetic acid. After 60 minutes at room temperature the reaction mixture was filtered off on celite, diluted with 300 ml of chloroform and washed with water. The red aqueous solution containing 4'-epidaunorubicin (VII) was separated and extracted with chloroform in order to eliminate the aglycones. Then the aqueous solution was adjusted to pH 8.6 and repeatedly extracted with chloroform. The combined chloroform extracts were dried over Na$_2$SO$_4$, concentrated to a small volume and acidified to pH 4.5 with 0.1 N methanolic hydrogen chloride to allow crystallization of 4'-epidaunorubicin hydrochloride (VII).

EXAMPLE 6

4'-Keto-N-trifluoroacetyldaunorubicin (III a) and

3'-epi-4'-keto-N-trifluoroacetyldaunorubicin (IV a)

To a mixture of 60 ml of methylene chloride and 5 ml of anhydrous dimethyl-sulfoxide cooled to below −60° C., a solution of 4 ml trifluoroacetic anhydride in 10 ml of anhydrous methylene chloride was added over a period of 15 minutes. During the addition period a white precipitate formed. After 15 minutes at −60° C. a solution of 6.25 g of N-trifluoroacetyldaunorubicin (I) in 40 ml of anhydrous methylene chloride was added dropwise to the mixture at −60° C. over a period of 15 minutes. Then the reaction mixture was stirred at 60° C. for 30 minutes and treated with 9 ml of triethylamine while keeping the temperature at −60° C. The reaction mixture was poured into 300 ml of methylene chloride and washed with aqueous 0.1 N HCl, an aqueous saturated solution of NaHCO$_3$ and water. The organic phase, after being dried over Na$_2$SO$_4$ was evaporated to give a crude mixture of compounds (III a) and (IV a) which was purified by chromatography on a column of silica gel using the mixture chloroform: acetone (98:2 v/v) as the eluent to give 4.6 g of a mixture of (III a) and (IV a) in an approximate 1:1 ratio. FDMS [M+]: 621. PMR (CDCl$_3$): 1.38 and 1.45 (two d [equal intensity], CH$_3$-C-5', 4.01 and 4.03 (two s [equal intensity] CH$_3$O; 13.10 and 13.13 (two s [equal intensity], C-11-OH) and 13.90 and 13.97 $\delta$ (two s [equal intensity], C-6-OH).

Moreover a mixture of (III a) and (IV a) in the 1:1 ratio may also be obtained by simply filtering a chloroform solution of pure (III a) on a layer of silica gel buffered at pH 7 with M/15 phosphate buffer.

EXAMPLE 7

4'-Keto-N-trichloroethoxycarbonyldaunorubicin (III b) and

3'-epi-4'-Keto-N-trichloroethoxycarbonyldaunorubicin (IV b)

7.04 g of N-trichloroethoxycarbonyldaunorubicin (II) were oxidized as described in Example 6 to give a mixture of 4'-keto-N-trichloroethoxycarbonyldaunorubicin (III b) and 3'-epi-4'-keto-N-trichloroethoxycarbonyldaunorubicin (IV b).

EXAMPLE 8

3',4'-diepidaunorubicin (VIII)

A solution of 6 g of a mixture of 4'keto-N-trifluoroacetyldaunorubicin (III a) and 3'-epi-4'-keto-N-trifluoroacetyldaunorubicin (IV a), obtained following the procedure described in Example 6, in 600 ml of methanol was cooled at −10° C. and treated with 0.140 g of NaBH$_4$ dissolved in 20 ml of methanol. After ten minutes the reduction was complete, and the reaction mixture was neutralized with aqueous 0.1 N HCl, evaporated to a small volume (50 ml) under vacuum and diluted with 250 ml of methylene chloride. The organic solution, after being washed with water, was dried over Na$_2$SO$_4$ and evaporated to a residue. The residue (5.7 g) which is a mixture of 4'-epi-N-trifluoroacetyldaunorubicin (V a) and 3',4'-diepi-N-trifluoroacetyldaunorubicin (VI a) in a 1:1 ratio was chromatographed on a column of silica gel buffered at pH 7 with M/15 phosphate buffer using as eluant the solvent system chloroform-:acetone (96:4 v/v). Equal amounts (1.9 g) of V a and VI a were obtained. The hydrolysis of the N-protecting groups of (V a) and (VI a) was performed using the procedure described in Example 2 affording in quantitative yield, 4'-epidaunorubicin hydrochloride (VII) and 3',4'-diepidaunorubicin (VIII) m.p. 180°–181° (dec.) $[\alpha]_D^{25}+243.5°$ (c 0.05:methanol).

Variations and modifications can, of course, be made without departing from the spirit and scope of the invention.

Having thus described our invention what we desire to secure by Letters Patent and hereby claim is:

1. A process for preparing 4'-epi-daunorubicin.HCl (VII) and 3',4'-di-epidaunorubicin.HCl (VIII):

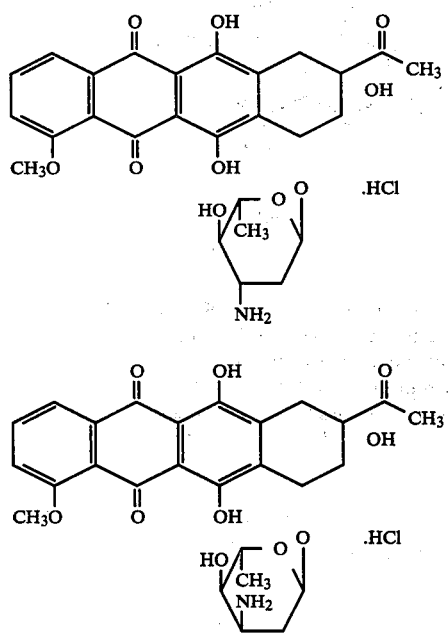

said process comprising subjecting N-trifluoroacetyl daunrorubicin (I):

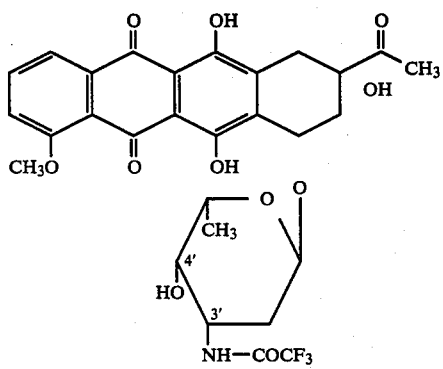

by treatment with dimethylsulfoxide activated by trifluoroacetic anhydride, to oxidation at the C-4' hydroxyl group at a temperature of about −65° to −60° C., followed by basification thereof with 1,5-diazobicyclo (4.3.0)-non-5-ene to form 4'-keto-N-trifluoroacetyl daunorubicin (III a):

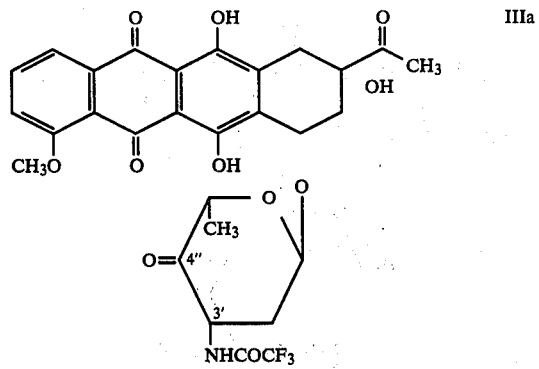

subjecting said 4'-keto-N-trifluoroacetyl daunorubicin (IIIa) to selective stereospecific reduction with sodium borohydride at a temperature of about −10° C. to obtain 4'-epi-N-trifluoroacetyl daunorubicin Va:

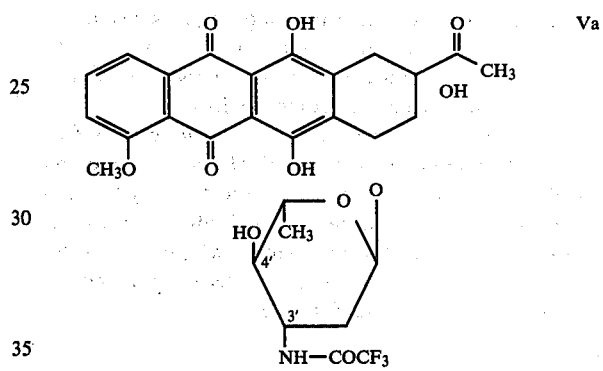

converting said 4'-epi-N-trifluoroacetyl daunorubicin (Va) to 4'-epi-daunorubicin base (VII) by treatment with a mild alkali to remove the N-trifluoroacetyl group and isolating said 4'-epi-daunorubicin as its hydrochloride or alternatively, subjecting said 4'-keto-N-trifluoroacetyl daunorubicin (IIIa) to epimerization by filtering a solution thereof through a column of silica gel buffered at pH 7 with M/15 phosphate buffer to give a 1:1 epimeric mixture of said (IIIa) and 3'-epi-4'-keto-N-trifluoroacetyl daunorubicin (IV a):

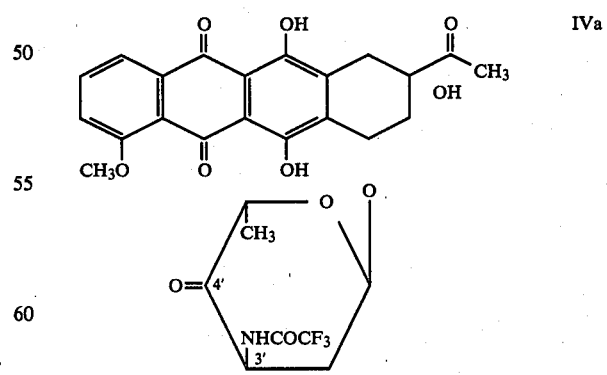

stereospecifically reducing said epimeric mixture with sodium borohydride as hereinabove described to obtain a 1:1 mixture of 4'-epi-N-trifluoroacetyl daunorubicin (Va) and 3'-4'-diepi-N trifluoroacetyl daunorubicin VI a:

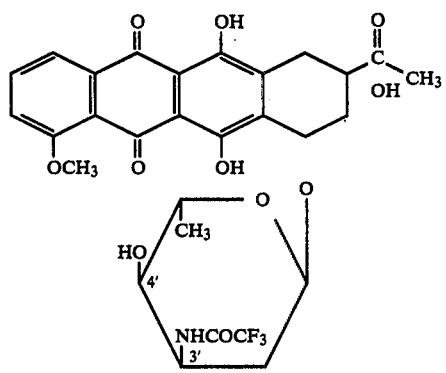

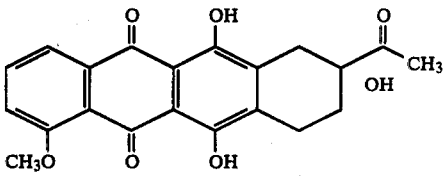

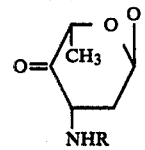

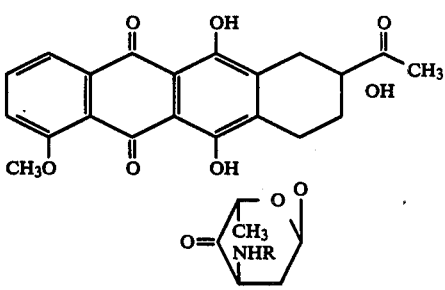

separating pure (VIa) from said mixture by chromatography on a column of silica gel buffered at pH 7 with M/15 phosphate buffer, removing the N-trifluoroacetyl group therefrom to obtain free 3',4'-diepi-daunorubicin base (VIII) and isolating same as the hydrochloride.

2. A process according to claim 1 wherein the N-trifluoroacetyl protecting groups are removed by hydrolysis with dilute aqueous sodium hydroxide.

3. A process according to claim 1 wherein the free bases of 4'-epi-daunorubicin (VII) and 3',4'-diepi-daunorubicin (VIII) are converted to their hydrochlorides by treatment with methanolic hydrogen chloride.

4. A process according to claim 1 wherein the selective stereospecific reduction is effected in methanol.

5. A compound of the formulae:

wherein R is —COCF$_3$ or —COOCH$_2$CCl$_3$.

6. A compound according to claim 5 which is 4'-keto-N-trifluoroacetyl daunorubicin.

7. A compound according to claim 5 which is 3'-epi-4'-keto-N-trifluoroacetyl daunorubicin.

* * * * *